US006907297B2

(12) United States Patent
Wellman et al.

(10) Patent No.: US 6,907,297 B2
(45) Date of Patent: Jun. 14, 2005

(54) EXPANDABLE INTRACARDIAC RETURN ELECTRODE AND METHOD OF USE

(75) Inventors: Parris S. Wellman, Hillsborough, NJ (US); Rajesh Pendekanti, Bridgewater, NJ (US); Jia Hua Xiao, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 446 days.

(21) Appl. No.: 10/032,296

(22) Filed: Dec. 21, 2001

(65) Prior Publication Data

US 2003/0065364 A1 Apr. 3, 2003

Related U.S. Application Data

(63) Continuation-in-part of application No. 09/966,765, filed on Sep. 28, 2001, now Pat. No. 6,695,838.

(51) Int. Cl.[7] .............................................. A61N 1/00
(52) U.S. Cl. ........................................................ 607/122
(58) Field of Search ............................ 607/4, 5, 14, 98, 607/99, 122, 123, 126, 129, 148; 600/374, 375; 606/41

(56) References Cited

U.S. PATENT DOCUMENTS

| | | | | |
|---|---|---|---|---|
| 5,311,866 A | * | 5/1994 | Kagan et al. | 600/374 |
| 5,697,928 A | | 12/1997 | Walcott et al. | 606/41 |
| 5,904,711 A | | 5/1999 | Flom et al. | 607/129 |
| 6,012,457 A | | 1/2000 | Lesh | 128/898 |
| 6,079,414 A | | 6/2000 | Roth | 128/898 |
| 6,161,543 A | | 12/2000 | Cox et al. | 128/898 |
| 6,164,283 A | | 12/2000 | Lesh | 128/898 |
| 6,179,832 B1 | | 1/2001 | Jones et al. | |
| 6,237,605 B1 | | 5/2001 | Vaska et al. | 128/898 |
| 6,245,064 B1 | | 6/2001 | Lesh et al. | 606/34 |
| 6,251,109 B1 | | 6/2001 | Hassett et al. | 606/45 |
| 2001/0051803 A1 | | 12/2001 | Desai et al. | |

FOREIGN PATENT DOCUMENTS

| | | |
|---|---|---|
| EP | 0 499 491 | 8/1992 |
| EP | 1 064 886 | 1/2001 |
| WO | WO 97/25916 | 7/1997 |

OTHER PUBLICATIONS

Javier Roman–Gonzalez et al. "Collateral Tissue Injury Occurring During Intrapericardial Catheter Ablation in the Closed Chest Canine Model." North American Society for Pacing and Clinical Electrophysiology 22nd Annual Scientific Sessions, Hynes Convention Center, Boston, Massachusetts, USA, pp. 388:(May 2–5, 2001).

David E. Haines et al. "Rapid, Continuous and Transmural Linear Ablation With a Novel Bipolar Radiofrequency Ablation System" North American Society for Pacing and Clinical Electrophysiology 22nd Annual Scientific Sessions, Hynes Convention Center, Boston, Massachusetts, USA, pp. 279:(May 2–5, 2001).

* cited by examiner

*Primary Examiner*—George Manuel
(74) *Attorney, Agent, or Firm*—Nutter, McClennen & Fish, LLP (57) ABSTRACT

A method of forming a lesion at a predetermined heart location is provided. An energy-delivering electrode is positioned proximal to the predetermined heart location; a return electrode is positioned in contact with cardiac tissue. An electrosurgical current, capable of delivering energy through the energy-delivering electrode to the predetermined heart location at a magnitude and for a duration effective to form a lesion is established. A system for treating atrial fibrillation by forming transmural lesions and a heart-positioning device including a return electrode are also provided. In one embodiment, one of the electrodes includes at least a portion that is selectively movable between a first, retracted position in which the electrode is adapted to be deployed through tissue, and a second, expanded position in which the electrode is adapted to be placed within a chamber of a heart.

20 Claims, 10 Drawing Sheets

EXPANDABLE INTRACARDIAC RETURN ELECTRODE AND METHOD OF USE

CROSS REFERENCE TO RELATED APPLICATIONS

This application is a continuation-in-part of U.S. patent application Ser. No. 09/966,765, filed Sep. 28, 2001, now U.S. Pat. No. 6,695,838, entitled "System and Method for Performing Cardiac Tissue Ablation."

FIELD OF THE INVENTION

This application relates to systems and methods for ablating cardiac tissue. More particularly, it relates to systems and methods for the treatment of atrial fibrillation.

BACKGROUND OF THE INVENTION

Cardiac arrhythmias, such as atrial fibrillation, are commonly occurring disorders characterized by erratic beating of the heart. The regular pumping function of the atria is replaced by a disorganized, ineffective quivering caused by chaotic conduction of electrical signals through the upper chambers of the heart. Atrial fibrillation may be caused by the rapid and repetitive firing of an isolated center or focus within the atrial cardiac muscle tissue. Such foci may act to trigger AF or may, once triggered, sustain the fibrillation. Recent studies have suggested that foci for such arrhythmia are predominantly in a region of cardiac tissue proximal to the pulmonary veins that extend out of the heart from the left atrium. More particularly, tissue proximal to the superior pulmonary veins denoted as ostia are likely AF foci.

While medication can be an effective treatment for some cases, many patients are not responsive to medical therapies and require alternative treatment. As an alternative to medication, a surgical technique, known as the Maze technique, requires open chest surgery to strategically incise the atrial wall, and subsequently repair the incisions by suturing. The result of this surgery is to create scar tissue located along the incision lines and extending through the atrial wall to block electrical conductivity from one segment to another.

While the Maze procedure has proven effective in restoring normal sinus rhythm, it requires considerable prolongation of cardiopulmonary bypass and aortic crossclamp time, especially when performed in combination with other open heart procedures. Over the last decade, more simplified techniques have been proposed which replace surgical incisions with ablations, or scars, formed in the heart tissue. The various energy sources used in ablation technologies include cryogenic, radiofrequency (RF), laser, and microwave energy. The ablation devices are used to create tissue lesions in an affected portion of the heart in order to block electrical conduction.

One common ablation technique employs the use of a catheter that is introduced into the heart (e.g., intravascularly) to direct RF energy at specific areas of heart tissue found to be the source of the irregular rhythms. An electrophysiology (EP) study is first performed to discover the location and characteristics of the arrhythmia and, once the specific location is identified and mapped, RF energy is delivered to the tissue to ablate the tissue, thus forming a lesion that blocks electrical conduction. While minimally invasive techniques are usually preferred, the procedure is often performed in combination with other open heart procedures as a prophylactic to prevent post-operative onset of atrial fibrillation.

RF ablation techniques are typically successful in treating atrial fibrillation, however the lesions must be well defined within the heart to be effective. The lesion must have a sufficient length, continuity and/or depth to interrupt or to block electrical conduction across the affected portion of the heart. This can be difficult to achieve without forming an incision in the atrium. In addition, if the energy is not uniformly transmitted to the target site, hot spots can form, possibly leading to severe tissue damage or blood coagulation (clots).

One potential problem that may be encountered during cardiac ablation procedures is the risk of collateral tissue damage. In some cases the energy-delivering electrode performing the ablation is positioned at the purported focus and a pad, which acts the return electrode, is externally placed on the patient's body. Although most of the generated energy may be appropriately directed at the focus, the uncertain, unpredictable energy return path from the heart to the return electrode pad may lead to damage of other vital organs or structures. The esophagus, the lungs, and nerve tissue are examples of organs or tissue structures that may be susceptible to unintended energy influx.

Accordingly, there exists a need for ablation systems and methods that can be used safely and effectively to effect cardiac ablation procedures.

SUMMARY OF THE INVENTION

The present invention provides ablation systems and methods for treating atrial fibrillation utilizing RF energy. The system comprises an active, energy delivering electrode and a return electrode that is placed in contact with tissue (e.g., cardiac tissue) within the patient's body. The use of such a system and method of the present invention is advantageous because it facilitates safe and effective ablation procedures in which the dispersion of current is controlled so as to minimize the potential for causing unintended collateral damage to non-target, sensitive tissue structures and organs.

According to a method of the invention, the return electrode is positioned in contact with tissue (e.g., cardiac tissue) within the patient's body. With the return electrode properly secured and placed to provide a controlled path for current, the energy-delivering electrode is positioned proximal to a part of an organ (e.g., the heart) where it is desired to effect ablation. An electrosurgical current is then established through the target tissue, between the energy-delivery electrode and the return electrode. The current should be delivered at a magnitude and for a duration effective to form a lesion that is sufficient to block electrical conductivity at the focus or foci. Preferably, the lesion is transmural, extending through the wall of the heart at the target site from an endocardial surface to an epicardial surface thereof, and it is continuous along its length. In one embodiment, the return electrode has a surface area that is larger than a surface area of the energy-delivering electrode.

An electrosurgical generator is used with the method of the invention to deliver current to the target tissue. The generator can be one that is able to operate in the bipolar and/or monopolar modes.

In one aspect, the target tissue is a surface segment of a portion of the heart, such as the left atrium. More particularly, the target tissue may be adjacent to a pulmonary vein ostium. The invention provides sufficient flexibility that the energy delivering and return electrodes can be placed in contact with or adjacent to target tissue that is on either an epicardial or endocardial surface of the heart. Moreover, the method may be utilized by accessing the target tissue through a sternotomy, through a thoracoscopic portal, or by other techniques. The method may be performed upon a beating heart or upon a stopped heart.

The return electrode that is utilized with the invention may take a variety of forms. In one aspect, the return electrode is of a patch-like shape that is able to be affixed by various techniques to the appropriate tissue in the patient's body. Alternatively, the return electrode can be attached to or integral with another tool or device that is utilized by the surgeon and which is in intimate contact with the patient's tissue (e.g., the heart) during the surgical procedure. For example, the return electrode may be attached to or integral with a heart positioning or manipulation device that is used to spatially manipulate the heart during a surgical procedure.

In other embodiments, one of the electrodes includes at least a portion that is selectively movable between a first, retracted position in which the electrode is adapted to be deployed through tissue, and a second, expanded position in which the electrode is adapted to be placed within a chamber of a heart. The invention further contemplates systems and devices that facilitate the practice of the invention.

BRIEF DESCRIPTION OF THE DRAWINGS

The invention will be more fully understood from the following detailed description taken in conjunction with the accompanying drawings, in which.

DETAILED DESCRIPTION OF THE INVENTION

In one aspect, the invention provides a method and system useful to safely and effectively ablate tissue. The system includes energy-delivering and return electrodes that are designed and oriented to enable the current pathways to be more predictable, thus eliminating the risk of collateral damage to heat- and current-sensitive tissue structures and organs that may result from stray current pathways. For example, in the case of ablation of heart tissue, the present invention enables current to travel through cardiac tissue and between the electrodes, thus avoiding heat-current-sensitive tissue and organs such as the lungs and the esophagus.

Although the invention is primarily described with respect to the ablation of cardiac tissue, one of ordinary skill in the art will recognize that the invention is also applicable to ablation procedures conducted on other organs and tissues.

Figure 1:
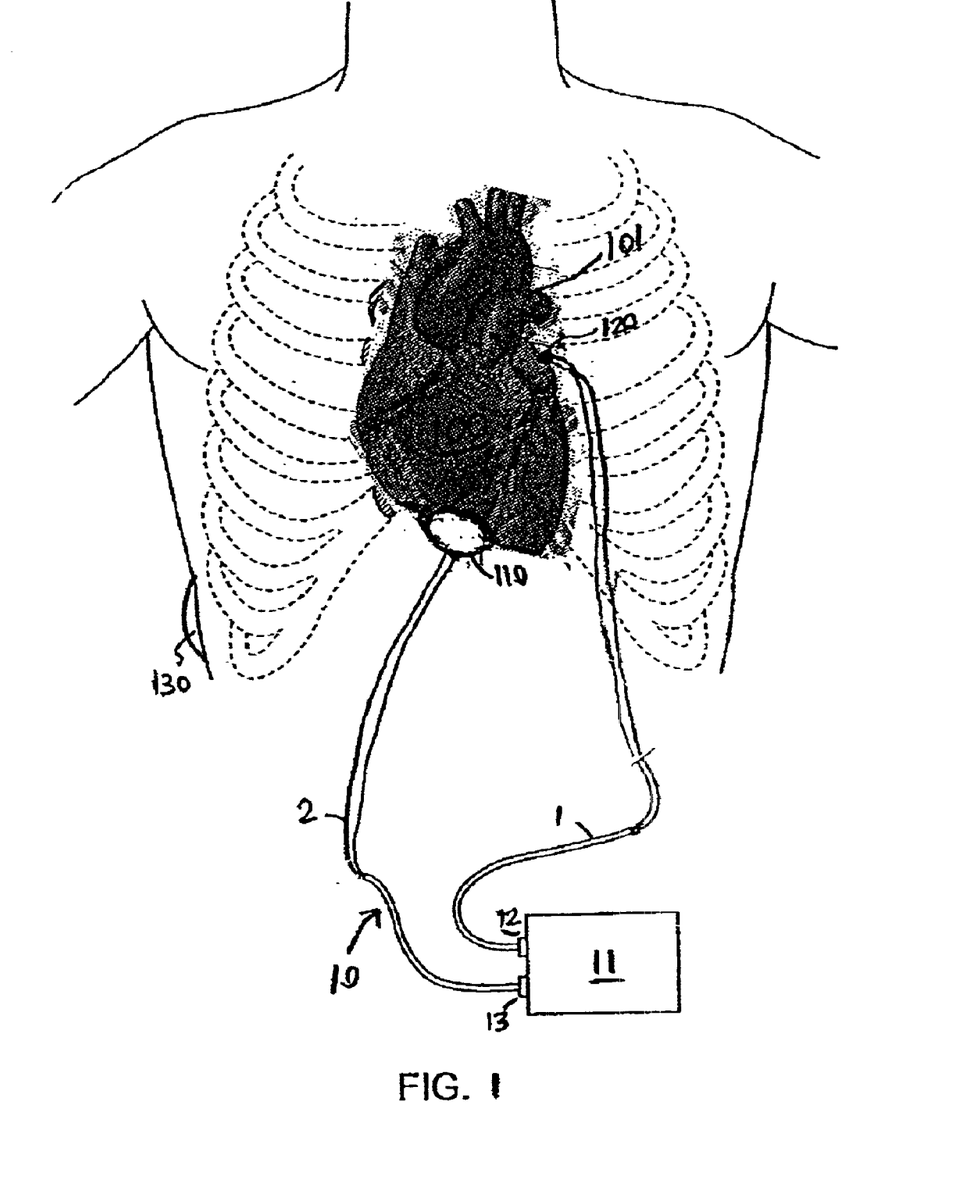
FIG. 1 is a schematic representation of a system according to one embodiment of the invention, useful to treat atrial fibrillation.

As shown in FIG. 1, system 10 is has an energy-delivering electrode 120 which communicates with one terminal 12 of an energy source 11 through conductor 1. The system 10 also includes a return electrode 110 that communicates with another terminal 13 of energy source 11 through conductor 2.

Energy delivering electrode 120 may take a variety of forms. Generally, virtually any type of conductive element can be used as the energy delivering electrode, provided that it is capable of accessing the desired target tissue (e.g., in the heart) and delivering electrosurgical current to a specific tissue location. The exact design of the energy-delivering electrode will vary depending on whether it is to be used in an open chest surgical procedure, a thoracoscopic surgical procedure, or in another type of surgical approach.

Figure 2:
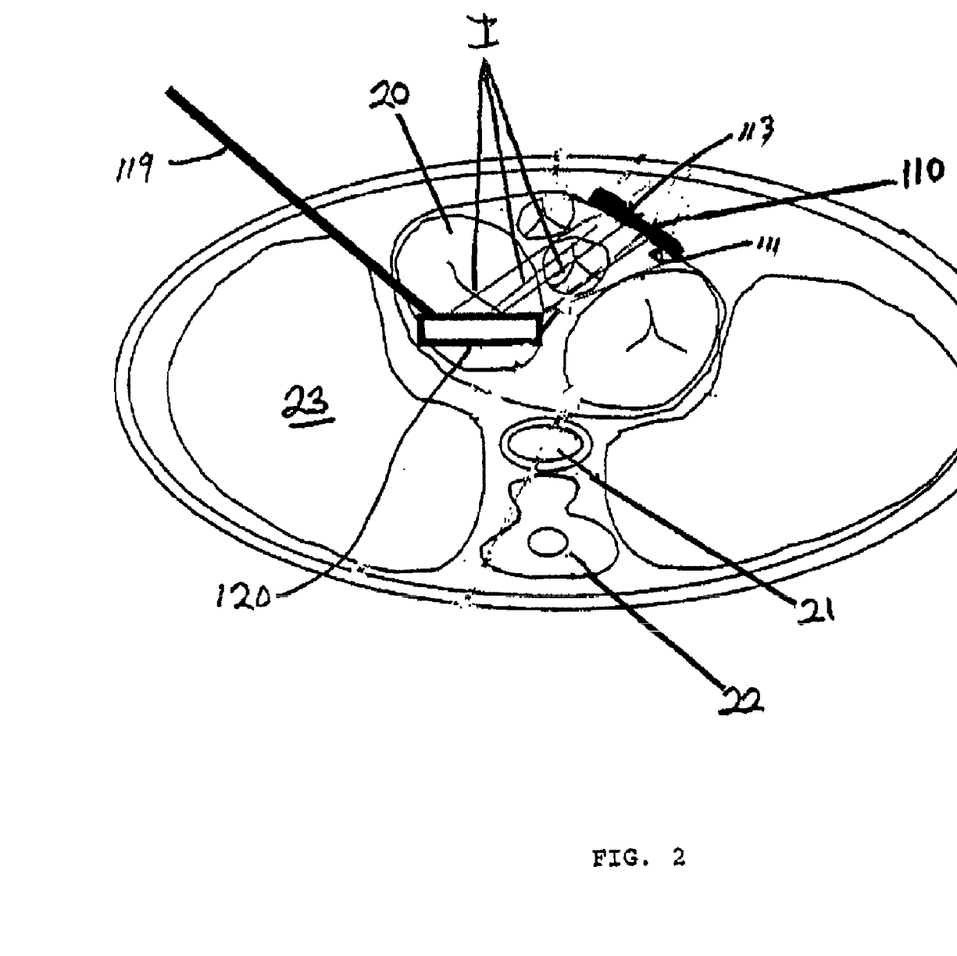
FIG. 2 is a cross-sectional view of the human body, in the axial plane, schematically illustrating one embodiment of the system of the invention.

FIG. 2 illustrates one embodiment of an energy-delivering electrode 120 that includes an elongate handle 119 having an electrode member 120 at its distal end. The handle 119 and/or the electrode member 120 can be flexible and/or malleable. Further, the handle may be constructed such that the distal end of the handle and/or the electrode 120 can be selectively deflected by the surgeon. At least a portion of the electrode member 120 can be formed from an electrically conductive material. In one embodiment useful for an epicardial or endocardial ablation of cardiac tissue through an open chest procedure, the electrode 120 has a conductive surface area in the range of about 2 to 100 mm$^2$. One having ordinary skill in the art will appreciate that minor modifications can be made to adapt the energy-delivering electrode 120 for ablation procedures conducted through thoracoscopic approaches or other minimally invasive surgical approaches. That is, the conductive element should be disposed at the distal end of an elongate element that is of a size and shape to enable it to be delivered to the surgical site through a thoracoscopic portal or through another access port. The elongate handle may be flexible or malleable to enable the energy-delivering electrode to be oriented and positioned in a desired manner. Alternatively or in addition, the distal end of the element that includes electrode 120 may be capable of selective articulation with respect to the elongate element. The surface area of the energy-delivering electrode useful in a thoracoscopic approach should be in the range of about 2 to 50 mm$^2$.

In an exemplary embodiment (not shown), the electrode member 120 can include an electrode array having several distinct electrode elements. Each distinct electrode element is adapted to communication with a source of ablative energy. In use, each distinct electrode element can be activated individually to transmit ablative energy to the return electrode. While the size and shape of the distinct electrode elements can vary, each distinct electrode element preferably has a surface area that is less than the total surface area of the electrically conductive portion of the return electrode.

The energy-delivering electrode 120 can be made from a variety of suitable materials that are both conductive and biologically compatible. Examples of such materials include titanium, titanium alloys (including nickel-titanium alloys), and stainless steels.

Figure 3:
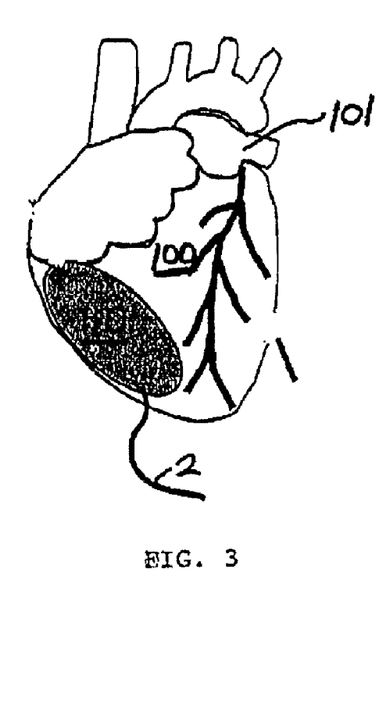
FIG. 3 is a plan view of a return electrode in contact with cardiac tissue according to one aspect of the invention.

In one embodiment the return electrode 110 may be a patch-like member as shown in FIGS. 1–3. The return electrode should have a conductive surface area that is greater than that of the energy-delivering electrode 120. Preferably, the tissue contacting conductive surface area of the return electrode should be about 10 to 100 times greater than the conductive surface area of the energy-delivering electrode. In one embodiment the return electrode 110 has a tissue contacting conductive surface area in the range of about 30 to 1000 $mm^2$.

As illustrated, the patch-like return electrode 110 can be a substantially planar member that is able to conform to and remain in contact with cardiac tissue within a patient's body cavity as shown in FIGS. 1–3. Alternatively, the patch-like return electrode can have a contoured surface that optimizes its ability to mate with a certain type of organ or tissue within a patient's body. The return electrode 110, or portions thereof, should be flexible and/or malleable to enable it to conform to the tissue against which it is placed. Although the return electrode 110 is shown to be in contact with tissue on the epicardial surface of the heart, it can be in contact with the endocardial surface of the heart, or other cardiac tissue such as the pericardium.

The return electrode 110 may have a conductive tissue contacting surface 111 and an opposed non-conductive surface 113 (FIG. 2). The non-conductive surface 113 can be formed from an insulator and/or a non-conductive material such as a biologically compatible polymer or fabric. Examples of such materials include expanded PTFE, polypropylene mesh, nylon, and polyester. The conductive surface 111 can be formed from a material that is both conductive and biologically compatible. The conductive material can be embedded within or otherwise affixed to the non-conductive surface 111. In another embodiment, the return electrode 110 is a conductive plate-like member that is covered on the surface 113 with a non-conductive material.

Examples of conductive materials from which the return electrode 110, or tissue contacting surface 111, can be made include a conductive composite material (e.g., conductive polyvinylidene fluoride or carbon loaded ultra-high molecular weight polyethylene), stainless steel, titanium, platinum, gold, silver, iridium, and alloys thereof. The conductive material may take the form of a continuous sheet or it may be formed from one or more wires, a mesh, a coil, or a braid.

The return electrode 110 may be secured to the desired patient tissue by a variety of techniques. By way of example, the return electrode can be secured to tissue using a temporary, biocompatible adhesive. Alternatively, it can be secured using compression, sutures, clamps or clips, or other mechanical fasteners. Examples of suitable adhesives include hydrocolloid adhesives (available from 3M) and other pressure sensitive adhesives.

In another embodiment, the return electrode may be attached to or integrally formed with another device that is used during the applicable surgical procedure. In the case of heart surgery and procedures involving the ablation of heart tissue (either open chest or thoracoscopic), various positioning devices are utilized to manipulate, move, and reposition the heart during the procedure. Such devices, e.g., heart lifters and positioners, may have attached to a heart contacting surface thereof one or more return electrodes. Alternatively, the return electrode(s) can be integrally formed with such devices. A return electrode design of this type offers the advantage of enabling a surgeon to spatially manipulate the heart with the same device that serves as the return electrode. This ensures good contact of the return electrode with the heart, and the return electrode can be positioned at any desired location on the heart.

Figure 4:
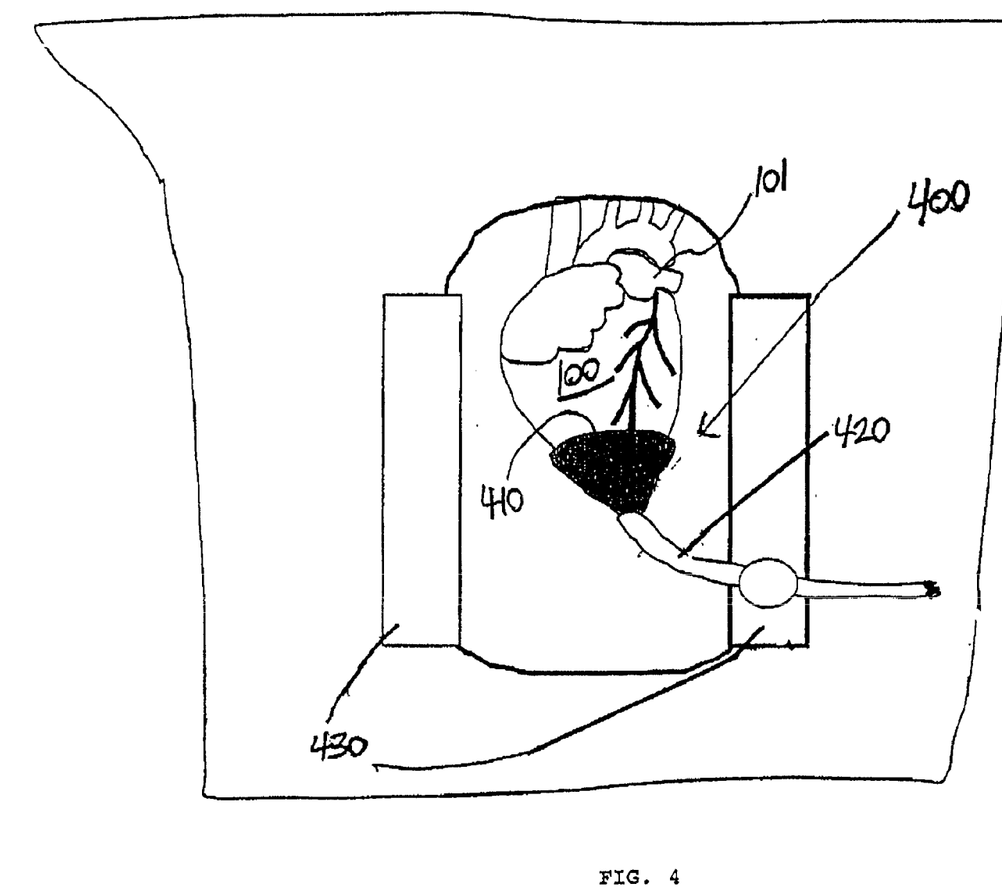
FIG. 4 is a plan view of a the system of the invention utilizing a heart-positioning device as a return electrode.

FIG. 4 illustrates one example of a heart manipulating device that also includes a return electrode. The apical lifter 400 shown in FIG. 4 includes a return electrode 410 that is formed on a tissue contacting surface of the apical lifter 400. The return electrode 410 may be integrally formed with the apical lifter, or it may be attached to the inner surface of an existing apical lifter. Further, the return electrode may be circumferentially formed within the inner surface of the apical lifter, it may be in the form of one or more strips disposed with the apical lifter, or it may be a conductive element that occupies all or part of the inner surface of the apical member. The return electrode 410 communicates with an energy source (not shown) through a conductor 420.

FIG. 4 shows an apical lifter modified to include a return electrode used in conjunction with open chest surgery wherein retractor blades 430 help to maintain access to the surgical site. In the illustrated embodiment, the apical lifter 400 is secured to the apex of the heart. A variety of techniques can be used to secure such a device to the heart, including compression, suction, biocompatible adhesives (including hydrocolloid adhesives), sutures, clamps or clips and other mechanical fasteners.

Such a device may also be used during a thoracoscopic procedure by providing, for example, an apical lifter or another type of heart manipulating device that is of a first size and shape sufficient to enter a patient's body through a thoracoscopic portal before deployment and a second size and shape following deployment in the body. One of ordinary skill in the art will readily appreciate that the size and shape of such a device may be altered by various techniques, such as by inflation following deployment and/or the use of a shape memory material. Apical lifter 400 may use suction to adhere to apex 440 of heart 100 in order to effect spatial manipulation of heart 100.

Although an apical lifter is the only illustrated example of a heart manipulating device modified to be or include a return electrode, one of ordinary skill in the art will readily appreciate that a variety of other tools and devices may be so modified or constructed according to the principles described above.

One of the ordinary skill in the art will appreciate that any return electrode according to the present invention, not just one associated with a heart manipulating device, may be constructed to enlarge upon deployment within a patient's body. That is, the return electrode may have a first, smaller size and shape before deployment to facilitate easy access to the surgical site, and a second, larger size and shape after deployment within the patient's body. Such a construction can be achieved by the use of a selectively inflatable return electrode, or one that is constructed of a shape memory material.

One of ordinary skill in the art will appreciate that a variety of electrosurgical generators can be used as the energy source 11. In one embodiment, the energy source is a radiofrequency (RF) generator that can operate in bipolar and/or monopolar mode. Such a generator should be capable of delivering RF energy having from about 1 to 100 watts of power and a frequency in the range of about 1 KHz to 1 MHz. More preferably, however, the desired frequency is in the range of about 250 KHz to 600 KHz, and the desired wattage is in the range of about 10 to 50 watts. One example of a suitable energy source is the Pegasys bipolar generator, available from Ethicon Endo-Surgery. Typically, the lesions are formed by delivering the energy for a duration of about 2 to 40 seconds at a power of about 20 to 40 watts.

As noted above, the invention enables an essentially monopolar system to be used in a manner that minimizes the risk of collateral damage by stray current to sensitive tissue structures and organs (e.g., the lungs and esophagus) during an ablation procedure. However, the system may be used with a monopolar and/or bipolar generator system. Although the system utilizes a return electrode that is remote from the energy-delivering electrode, the return electrode is positioned within and in contact with organs or other tissue structures within the patient's body cavity. Preferably, the return electrode is in contact with cardiac tissue.

In one embodiment, the system is useful for ablation of tissue, such as cardiac tissue. In conducting such a procedure, the target tissue is surgically accessed in an appropriate manner (e.g., by open chest surgery or by a thoracoscopic approach) and the return electrode 110 is attached to tissue within the patient's body, in proximity to the target tissue. Preferably, the return electrode is attached to a portion of the heart or other cardiac tissue such as the pericardium, and it is secured to tissue so that the conductive surface area of the return electrode remains in contact with the tissue during the ablation procedure. The energy-delivering electrode 120 is then positioned proximal to, and preferably in contact with, the target tissue to be ablated. As shown in FIG. 1, the energy-delivering electrode 120 is placed on an epicardial surface of the heart, at a location close to a juncture (or ostium) with pulmonary vein 101. This location, within the left atrium of heart 100, is known to be a common atrial fibrillation (AF) focus, ablation of which is effective to block the electrical conduction responsible for the atrial fibrillation. Upon activation of the energy source, current is delivered to the tissue, between the energy-delivering electrode and the return electrodes 120, 100. The current is delivered for a duration of time and at a magnitude sufficient to form a fully transmural (i.e., completely through the heart wall) lesion which will disrupt the AF focus by blocking electrical conduction therein. As noted above, the current may be delivered at a power level of about 20–40 watts for about 2 to 40 seconds. The positioning of the electrodes as described above prevents the conductive pathways through which energy will travel from leaving the heart, thus minimizing the risk of collateral tissue damage by stray current. Use of a small active electrode produces sufficient current density to achieve ablation of tissue in proximity to the active electrode while ensuring that no other damage is done.

FIG. 2 illustrates likely return current paths (I) when the energy-delivering electrode 120 ablates tissue on the epicardial surface of the left atrium 20 with the return electrode attached to an epicardial surface of the right ventricle. As shown, return current paths (I) avoid current- or heat-sensitive structures such as the esophagus 21, spine 22, and lung 23 and tend to be confined to cardiac tissue located between the two electrodes. In this way, the return current paths (I) are less likely to cause collateral tissue damage.

As noted above, embodiments of the system described above may be used by surgeons accessing a patient's body through open chest surgery or by a thoracoscopic approach. Accordingly, type and size of the electrodes, and the method of attachment of return electrode may vary depending upon the requirements of a given application.

FIGS. 5A–9B illustrate alternative embodiments of a return electrode for use with an ablation system according to the present invention. In each embodiment, the return electrode is movable between a first, retracted position and a second, expanded position. The electrode is adapted to be deployed through tissue in the retracted position. Once inserted through the tissue and, for example, into a chamber of a heart, the electrode can then be moved to the expanded position. The active, energy-delivering electrode can then be utilized to ablate tissue disposed therebetween. The embodiments illustrated in FIGS. 5A–9B are intended to be exemplary, and one having ordinary skill in the art will understand that various alternative designs are likewise within the scope of the invention.

FIGS. 5A–5D illustrate one embodiment of a return electrode 30 disposed within an inner lumen 52 of an elongate cylindrical member 50. The elongate cylindrical member 50 can have virtually any shape and size, and can be, for example, a catheter or similar introducer element. The cylindrical member 50 preferably includes open, or at least partially open, proximal and distal ends 51, 53, and an inner lumen 52 extending therebetween. A person having ordinary skill in the art will appreciate that the return electrode 30 can be deployed to a surgical site using virtually any type of introducer element.

Figure 5A:
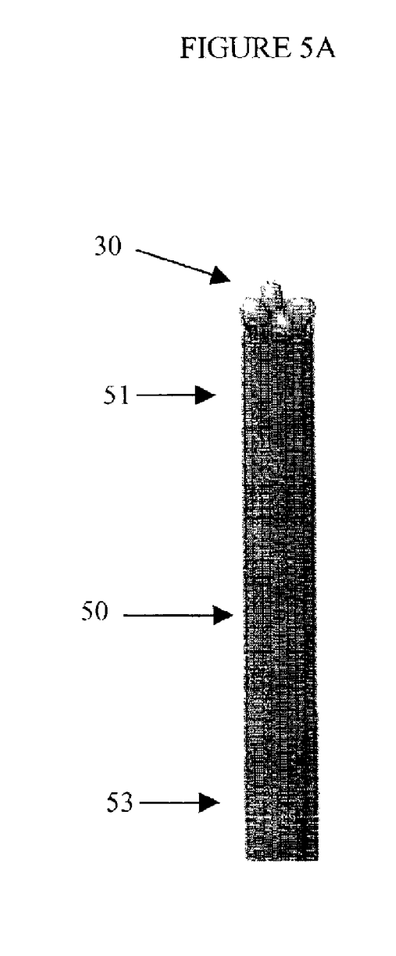
FIGS. 5A–5D illustrate one embodiment of an expandable element movable between a first condition and a second, expanded condition useful in a system for treating atrial fibrillation having.
Figure 5B:
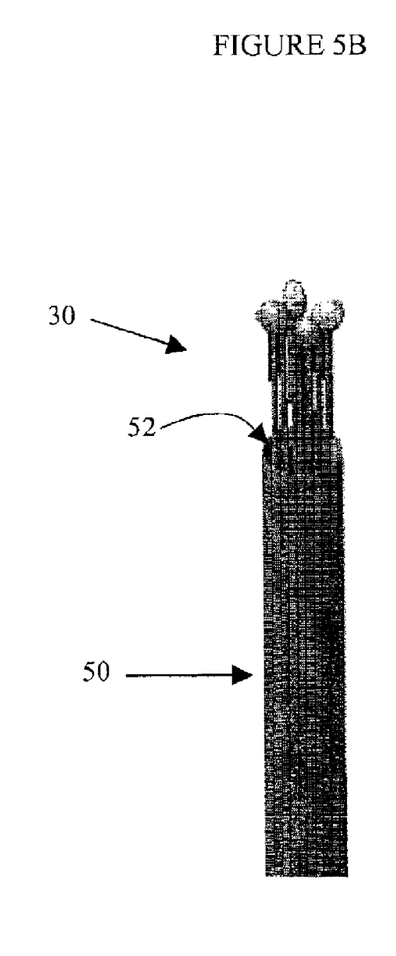
Figure 5C:
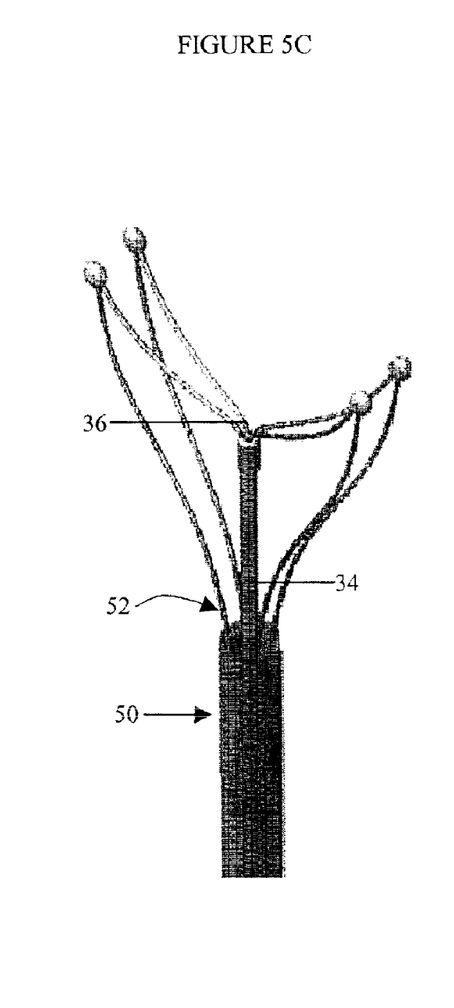
Figure 5D:
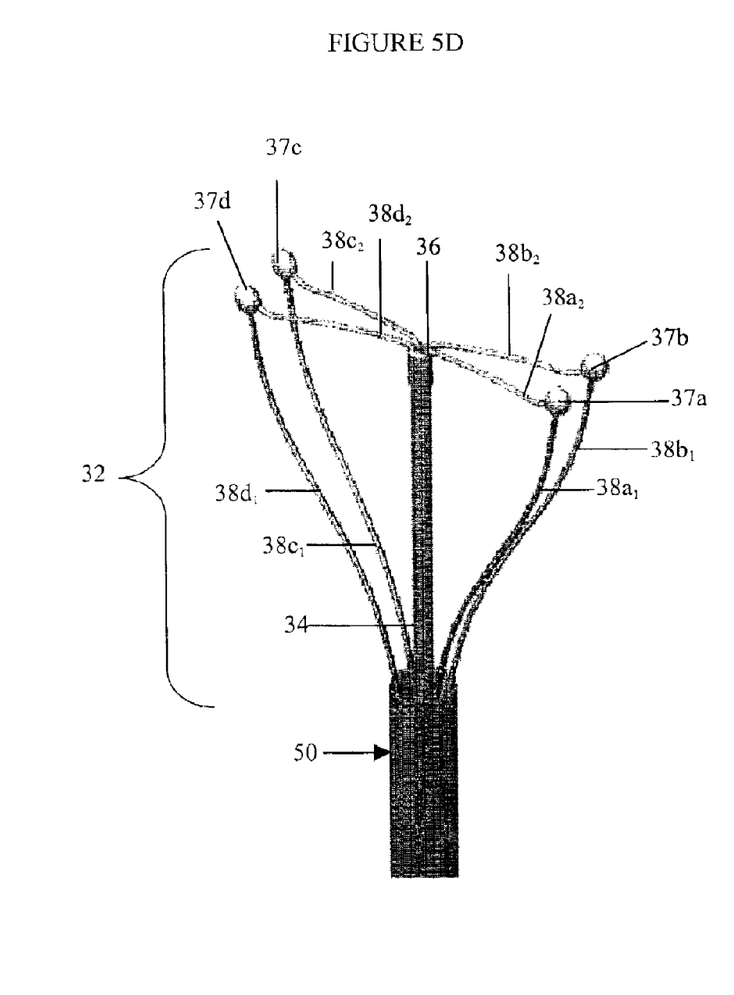

The return electrode 30, which is at least partially disposed within the inner lumen 52 of the elongate cylindrical member 50, has a generally elongate shape and includes a proximal portion (not shown) and a distal portion 32 (FIG. 5D). The distal portion 32 is movable between a first, retracted position, shown in FIG. 5A, in which the distal portion 32 is collapsed and substantially disposed within the inner lumen 52 of the elongate member 50, and a second, expanded position, shown in FIG. 5D, in which the distal portion 32 extends outwardly from the elongate member 50. FIGS. 5B and 5C illustrate the return electrode 30 in the partially retracted/expanded positions.

As shown in FIGS. 5C and 5D, the return electrode 30 includes a central rigid member 34 having a proximal end (not shown) and a distal end 36. Four conductive elements 37a, 37b, 37c, 37d are mated to the central rigid member 34 and are effective to receive ablative energy transmitted through tissue from an active electrode (not shown). The conductive elements 37a, 37b, 37c, 37d can have virtually any shape and size and can be, for example, solid spherical members, as shown in FIG. 5D. Preferably, the conductive members 37a, 37b, 37c, 37d have a combined surface area that is greater than a surface area of the active electrode (not shown).

The conductive elements 37a, 37b, 37c, 37d can be mated to the central rigid member 34 using a variety of mechanism, but preferably are mated via connector members 38. As shown, proximal and distal connector members $38a_1$, $38a_2$, $38b_1$, $38b_2$, $38c_1$, $38c_2$, $38d_1$, $38d_2$ extend from each conductive element 37a, 37b, 37c, 37d to mate the conductive element 37a, 37b, 37c, 37d to the central rigid member 34. The distal connector members $38a_2$, $38b_2$, $38c_2$, $38d_2$ extend between the conductive element 37a, 37b, 37c, 37d and the distal end 36 of the central rigid member 34, and the proximal connector members $38a_1$, $38b_1$, $38c_1$, $38d_1$ mate to the central rigid member 34 at a location proximal to the distal end 36 of the central rigid member 34.

The connector members $38a_1$, $38a_2$, $38b_1$, $38b_2$, $38c_1$, $38c_2$, $38d_1$, $38d_2$ can have virtually any size and shape, but are preferably wire-like members which are deformable to allow the return electrode 30 to be moved between the expanded and retracted positions. In an exemplary embodiment, each connector member $38a_1$, $38a_2$, $38b_1$, $38b_2$, $38c_1$, $38c_2$, $38d_1$, $38d_2$ is formed from a shape memory material such that, upon being extended from the cylindrical member 50, the connector members expand radially outwardly to assume an orientation such as that shown in FIG. 5D. The connector members $38a_1$, $38a_2$, $38b_1$, $38b_2$, $38c_1$, $38c_2$, $38d_1$, $38d_2$ can optionally be formed from a conductive material as well. A person having ordinary skill in the art will appreciate that, while four conductive elements 37a, 37b, 37c, 37d and eight connector members $38a_1$, $38a_2$, $38b_1$, $38b_2$, $38c_1$, $38c_2$, $38d_1$, $38d_2$ are shown, the return electrode 30 can have a variety of configurations.

In use, a proximal end (not shown) of the central rigid member 34 can be grasped and moved in proximal and distal directions to cause the return electrode 30 to move between the retracted and expanded positions. Movement of the central rigid member 34 in a distal direction will cause the return electrode 30 to extend from the distal end 51 of the elongate cylindrical member 50. The connector members $38a_1$, $38a_2$, $38b_1$, $38b_2$, $38c_1$, $38c_2$, $38d_1$, $38d_2$ will thus extend to the expanded position, shown in FIG. 5D. Conversely, proximal movement of the central rigid member 34 will force the connector members $38a_1$, $38a_2$, $38b_1$, $38b_2$, $38c_1$, $38c_2$, $38d_1$, $38d_2$ to deform and the return electrode 30 to move to the retracted position, shown in FIG. 5A.

A person having ordinary skill in the art will appreciate that the return electrode 30 can have a variety of configurations. For example, the distal connector members $38a_2$, $38b_2$, $38c_2$, $38d_2$ can extend through an inner lumen formed in the central rigid member 34 and out an open proximal end of the central rigid member 34. A force can be applied to the proximal portion of the distal connector members $38a_2$, $38b_2$, $38c_2$, $38d_2$ which extends out the open proximal end of the central rigid member 34 to move the return electrode 30 between the expanded and retracted positions. Movement of the return electrode 30 to the expanded position would cause the conductive elements 37a, 37b, 37c, 37d to be positioned at a distance from the distal end 36 of the rigid member 34. Conversely, movement of the return electrode 30 to the retracted position would cause the conductive elements 37a, 37b, 37c, 37d to abut the distal end 36 of the central rigid member 34.

Alternatively, or in addition, the proximal connector members $38a_1$, $38b_1$, $38c_1$, $38d_1$ can extend through the inner lumen of the elongate cylindrical member 50, adjacent the central rigid member 34, and out an open proximal end (not shown) of the cylindrical member 50. A force can be applied to the proximal end of the proximal connector members $38a_1$, $38b_1$, $38c_1$, $38d_1$ to assist in moving the return electrode between the expanded and retracted positions.

Figure 6A:
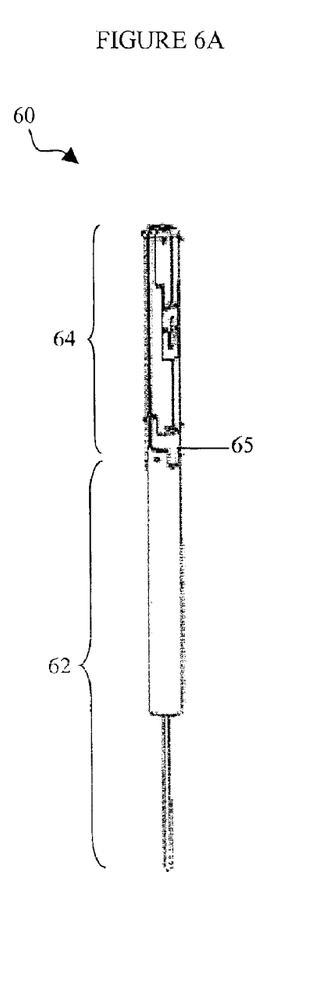
FIGS. 6A–6C illustrate another embodiment of an expandable element movable between a first condition and a second, expanded condition.
Figure 6B:
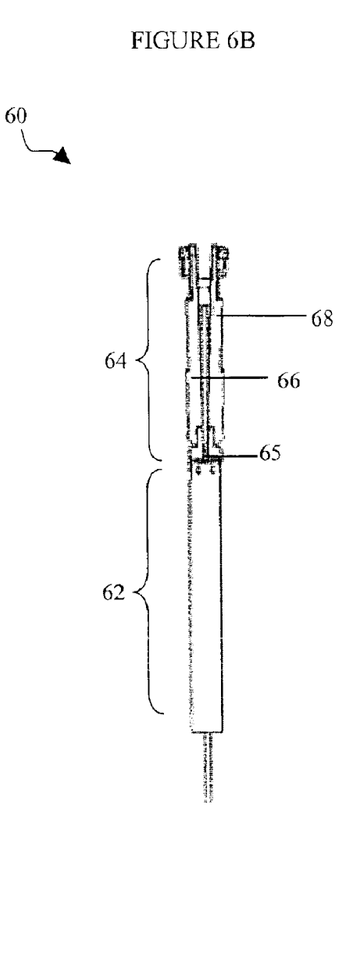
Figure 6C:
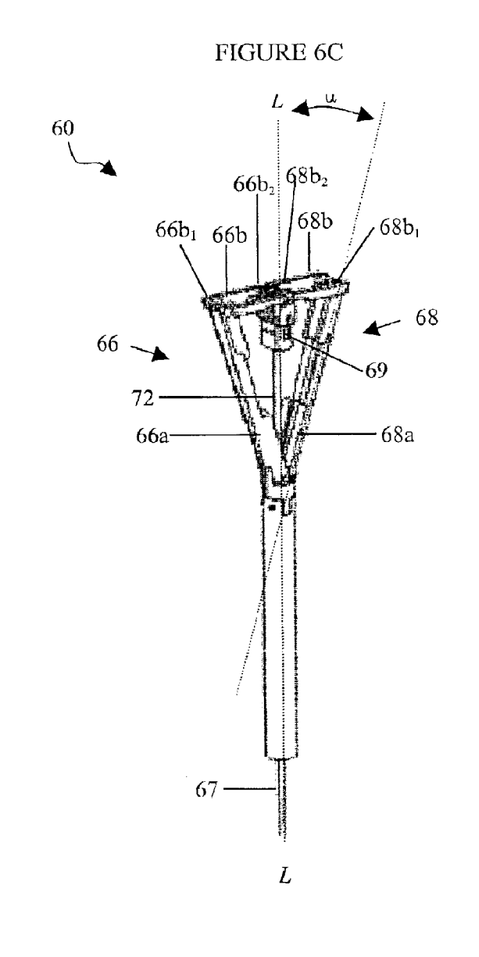

FIGS. 6A–6C illustrate another embodiment of a return electrode 60 having a rigid, or semi-rigid, proximal portion 62, and a distal portion 64 movable between a first, retracted position, shown in FIGS. 6A and 6B, and a second, expanded position, shown in FIG. 6C. The return electrode 60 has a generally elongate cylindrical shape in the retracted position, and a three-dimensional shape in the expanded position. The proximal portion 64 can have a variety of configurations, but is preferably an elongate cylindrical member having an inner lumen extending therethrough. The distal portion 64 is mated to the proximal portion 62 at a juncture 65. A variety of attachment mechanisms can be provided for mating the proximal and distal portions 62, 64. By way of non-limiting example, the proximal and distal portions 62, 64 can be welded, adhesively secured, or mechanically connected to one another. Preferably, the attachment mechanism is one that allows movement of the distal portion 64 with respect to the proximal portion 62.

The distal portion 64 of the return electrode 60 includes first and second expansion elements 66, 68. As shown in FIG. 6C, the expansion elements 66, 68 each include a proximal portion 66a, 68a, and a distal portion 66b, 68b. The proximal and distal portions 66a, 68a, 66b, 68b can have virtually any shape and size, but are preferably elongate members. At least a portion of each expansion member 66, 68 is formed from an electrically conductive material. The total surface area of the electrically conductive portions of the expansion members 66, 68 should be greater than a surface area of the active electrode (not shown).

The proximal portion 66a, 68a of each expansion member 66, 68 extends from the juncture 65 at an angle α with respect to the longitudinal axis L, and mates to a distal portion 66b, 68b of one of the expansion members 66, 68. While the angle α can vary, the angle α is preferably between about 20° and 70°, and more preferably is between about 30° and 50°. Preferably, the proximal portion 66a, 68a of each expansion element 66, 68 is pivotally mated to an outer end $66b_1$, $68b_1$ of one of the distal portions 66b, 68b. The inner ends $66b_2$, $68b_2$ of the distal portions 66b, 68b are preferably pivotally mated to each other. A central member 69 is mated to the inner end $66b_2$, $68b_2$ of each distal portion 66b, 68b, and is slidably disposed on an actuating member 67. The actuating member 67, e.g. a wire, extends from the central member 69, through the inner lumen and out an open proximal end of the proximal portion 62 of the return electrode.

In use, movement of the actuating member 67 in a proximal direction causes the central member 69 to slide proximally, thereby causing the distal portions 66b, 68b to move from a position in which the distal portions 66b, 68b are substantially perpendicular to the longitudinal axis L, shown in FIG. 6C, to a position in which the distal portions 66b, 68b are substantially parallel to the longitudinal axis L of the return electrode 60, as shown in FIGS. 6A and 6B. Movement of the actuating member 67 in a proximal direction also causes the proximal portions 66a, 68a of the expansion members 66, 68 to move inwardly toward the longitudinal axis L, as shown in FIG. 6C. Conversely, movement of the actuating member 67 in a distal direction causes the central member 69 to slide distally, thereby causing the distal portions 66b, 68b to move from a substantially parallel position, as shown in FIGS. 6A and 6B, to a substantially perpendicular position, as shown in FIG. 6C, and the proximal portions 66a, 68a of the expansion members 66, 68 to move outwardly away from the longitudinal axis L, as shown in FIGS. 6A and 6B.

A person having ordinary skill in the art will appreciate that a variety of actuating mechanisms can be utilized for moving the return electrode 60 between the retracted and expanded positions. For example, a lever can be provided for effecting movement of the expansions members. Alternatively, the expansion members can be formed from a shape memory material which is biased to the expanded position. In use, the return electrode 60 can be introduced into a region in the body through a catheter, whereby the return electrode 60 is retained in the retracted position by the catheter until the distal portion 64 extends through the catheter and into the desired region in the body. Proximal movement of the return electrode 60 will conversely cause the distal portion 64 to be disposed within the catheter, and thereby forced back into the retracted position.

Figure 7A:
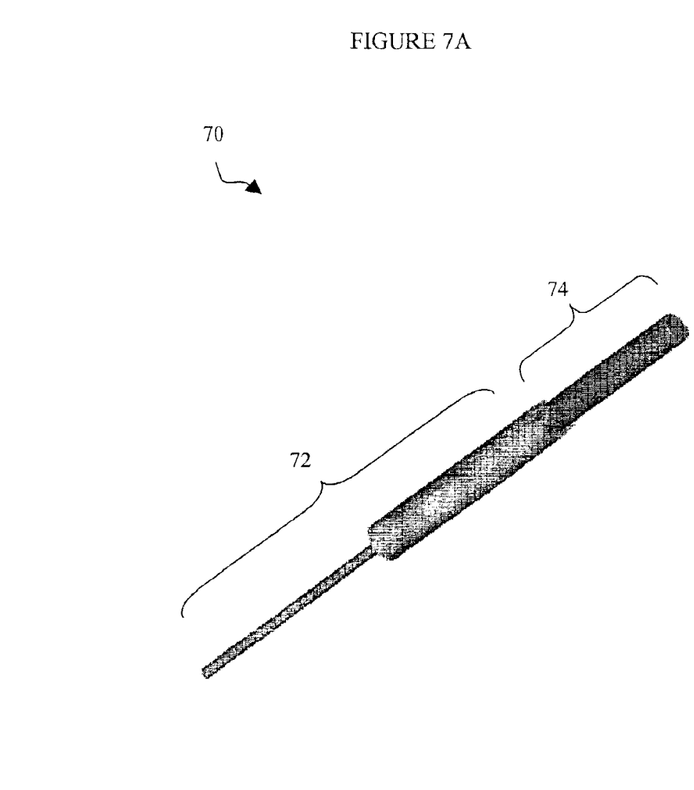
FIGS. 7A–7B illustrate yet another embodiment of an element movable between a first, retracted position, and a second, expanded condition that is useful in a system for treating atrial fibrillation.
Figure 7B:
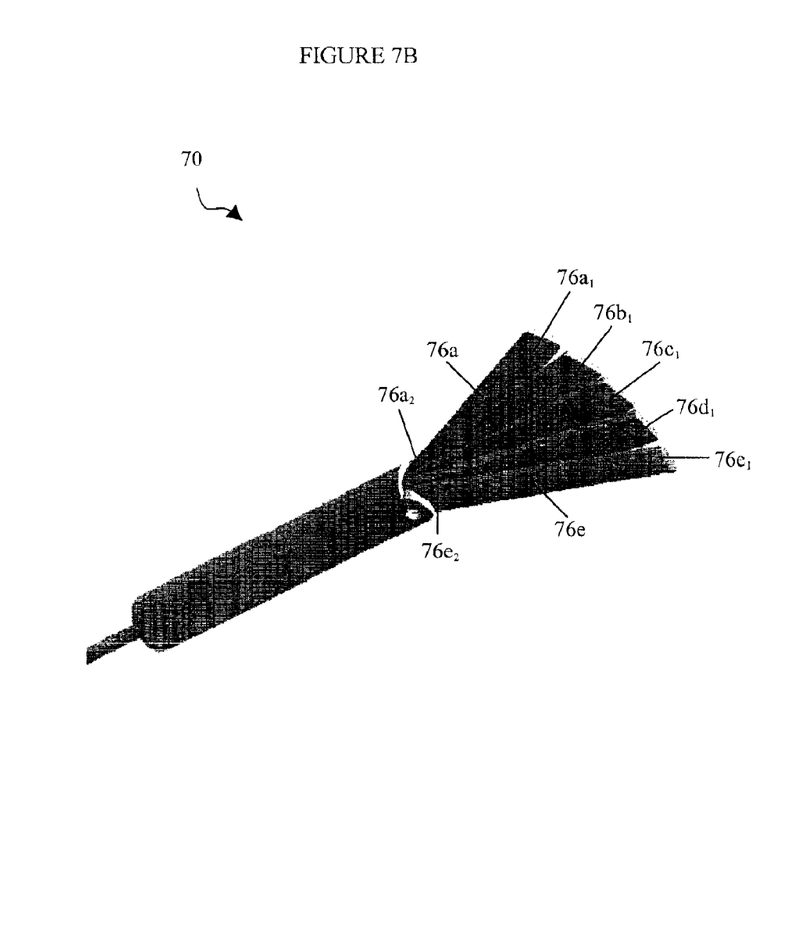

FIGS. 7A–7B illustrate yet another embodiment of a return electrode 70 according to the present invention. As shown, the return electrode 70 includes a proximal portion 72 and a distal portion 74. The proximal portion 72 can have a variety of configurations, but is preferably an elongate rigid member having an inner lumen (not shown) extending therethrough.

The distal portion 74 includes several conductive members 76a, 76b, 76c, 76d, 76e which are movable between a retracted position, shown in FIG. 7A, and an expanded position, shown in FIG. 7B. The conductive members 76a, 76b, 76c, 76d, 76e collectively have a generally elongate solid cylindrical shape in the retracted position, and have a substantially planar, fan-like shape in the expanded position. The proximal end $76a_2$, $76b_2$, $76c_2$, $76d_2$, $76e_2$ of each conductive member 76a, 76b, 76c, 76d, 76e is pivotally attached to the proximal portion 72 of the return electrode 70 with a securing device, such as a rivet or screw. A person having ordinary skill in the art will appreciate that the conductive members 76a, 76b, 76c, 76d, 76e can assume a variety of configurations, and can have virtually any shape and size.

An actuating member 78 extends from the proximal end $76a_2$, $76b_2$, $76c_2$, $76d_2$, $76e_2$ of each conductive member 76a, 76b, 76c, 76d, 76e, through the inner lumen of the proximal portion 72 of the return electrode 70, and emerges from the open proximal end of the proximal portion 72. The actuating member, e.g. a wire, is effective to move the conductive members 76a, 76b, 76c, 76d, 76e between the retracted and expanded positions. In use, applying a proximally directed force to the actuating member 78 will cause the conductive members 76a, 76b, 76c, 76d, 76e to move to the expanded position, shown in FIG. 7B, and applying a distally directed force to the actuating member 78 will cause the conductive members 76a, 76b, 76c, 76d, 76e to move to the retracted position. Alternatively, a biasing member (not shown), such as a spring, can be provided for biasing the conductive members 76a, 76b, 76c, 76d, 76e to one of the expanded or retracted positions, preferably to the retracted position. Thus, the force applied to the actuating member 78 will overcome the biasing member to effect movement of the conductive members 76a, 76b, 76c, 76d, 76e.

The conductive members 76a, 76b, 76c, 76d, 76e can be formed from a variety of materials. Preferably, at least a portion of each conductive member 76a, 76b, 76c, 76d, 76e is formed from an electrically conductive material. In one embodiment, each conductive member 76a, 76b, 76c, 76d, 76e can include a variety of discrete conductive elements (not shown) disposed thereon. Preferably, the conductive members 76a, 76b, 76c, 76d, 76e, or the conductive elements of each conductive member 76a, 76b, 76c, 76d, 76e, have a combined surface area that is greater than a surface area of the active electrode (not shown).

Figure 8A:
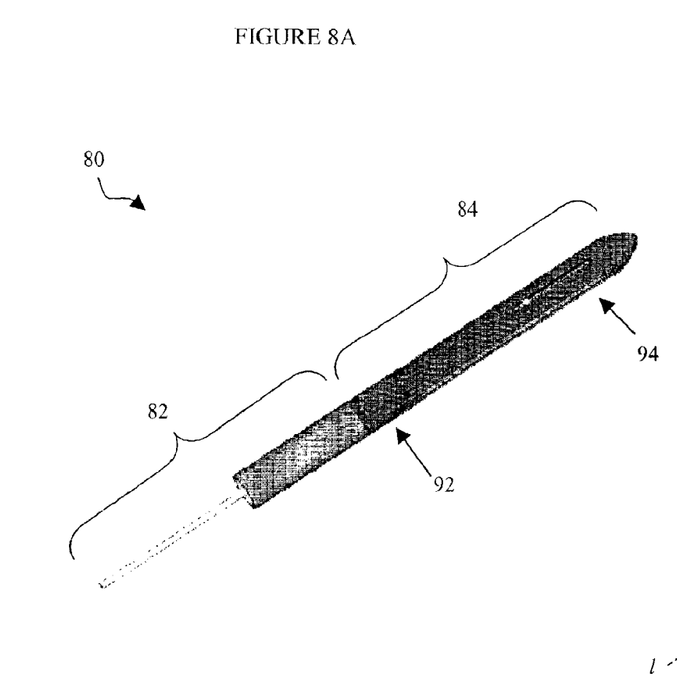
FIGS. 8A–8C illustrate a further embodiment of an element movable between a first condition and a second, expanded condition that is useful in a system for treating atrial fibrillation.
Figure 8B:
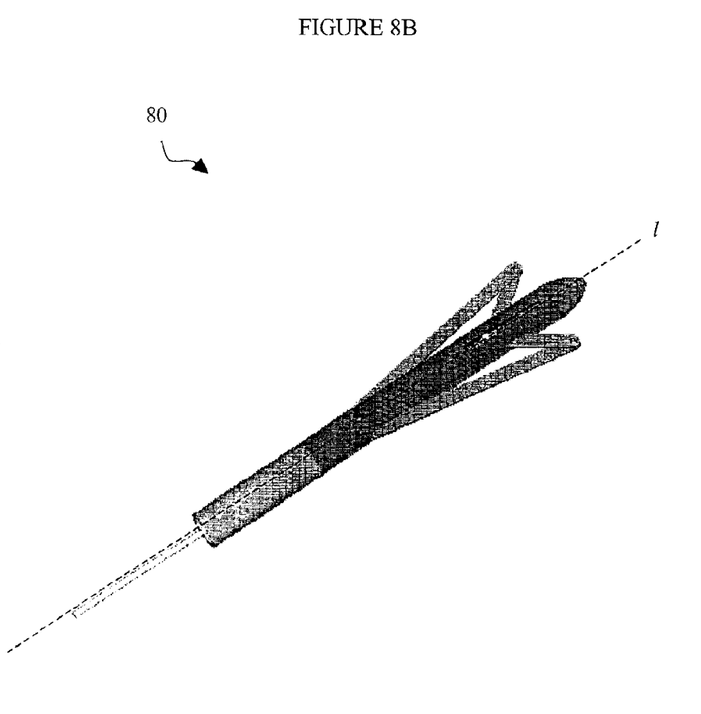
Figure 8C:
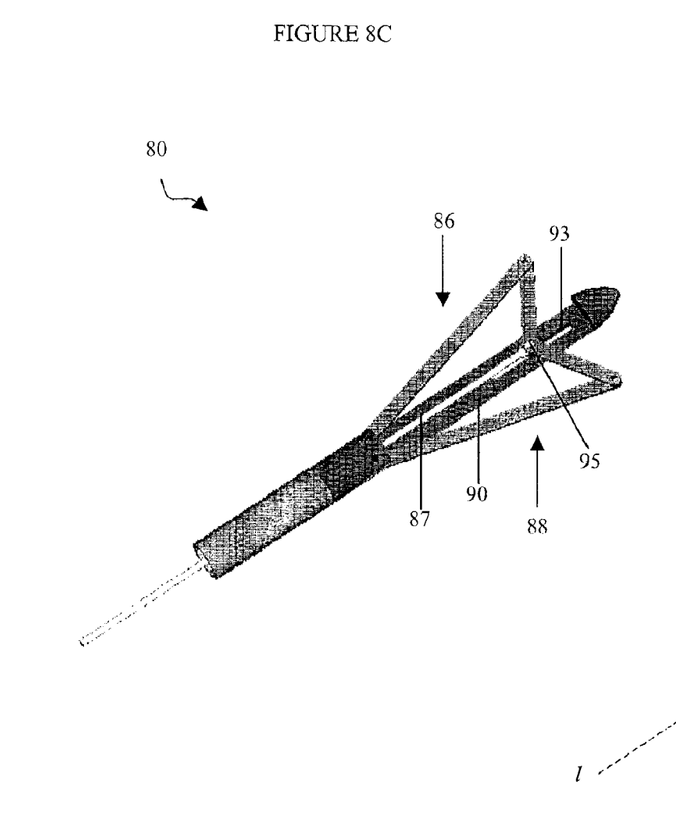
Figure 8D:
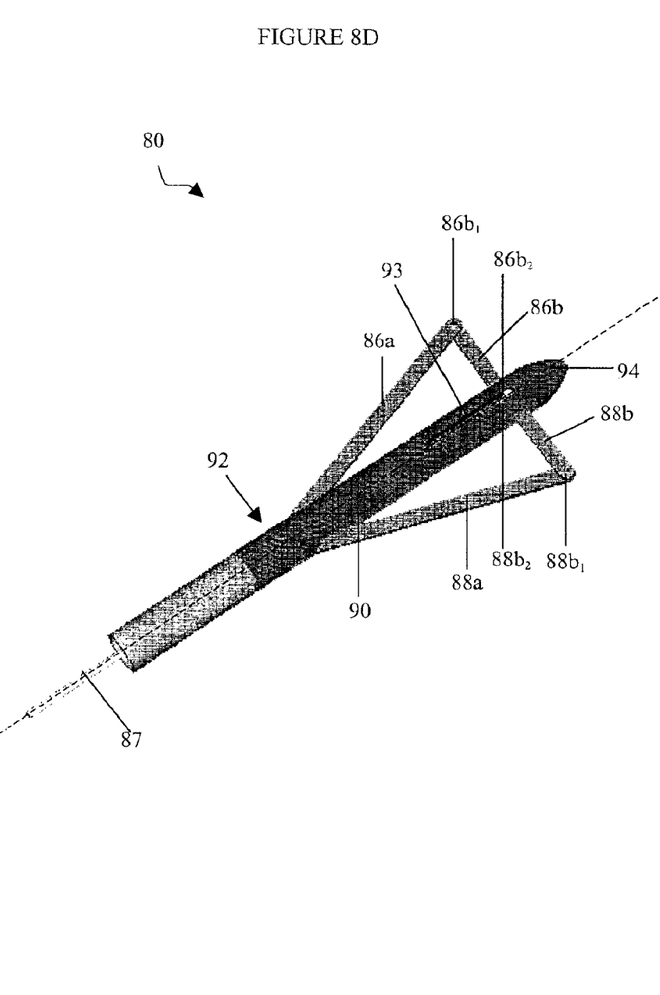

FIGS. 8A–8D illustrate another embodiment of a return electrode 80 having a proximal portion 82 and a distal portion 84. The return electrode 80 has a substantially elongate cylindrical shape in the retracted position, as shown in FIG. 8A, and has a substantially three-dimensional shape in the expanded position, as shown in FIGS. 8B–8D. The embodiment shown in FIGS. 8A–8D is similar to the embodiment shown in FIGS. 6A–6C, however, the return electrode 80 includes a distal extension 90 mated to the proximal portion 82. First and second expansion members 86, 88 are movably mated to the distal extension 90. A person having ordinary skill in the art will appreciate that all, or a portion of each expansion member 86, 88, and optionally, the distal extension 90 can be formed from an electrically conductive material.

The distal extension 90 is a substantially elongate member having a proximal end 92, a distal end 94, and an elongate slit 93 extending therebetween. While the size and shape can vary, the distal extension 90 preferably has a semi-circular elongate shape, as shown in FIG. 8C. The expansion members 86, 88 extend between the proximal and distal ends 92, 94 of the distal extension 90, and are preferably disposed on the flattened side of the semi-circular distal extension 90.

Each expansion member 86, 88 includes a proximal portion 86a, 88a, and a distal portion 86b, 88b. Each proximal portion 86a, 88a extends from the proximal end 92 of the distal extension 90, and pivotally mates to an outer end $86b_1$, $88b_1$ of one of the distal portion 86b, 88b. The proximal portion 86a, 88a of each expansion member 86, 88 extends in a direction outward from the longitudinal axis l of the return electrode 80 in the expanded position, and extends along the longitudinal axis l in the retracted position.

An inner end $86b_2$, $88b_2$ of each distal portion 86b, 88b is pivotally mated to an actuating member 87, which extends through an inner lumen (not shown) formed in the proximal portion 82 of the return electrode. A mating element 95, such as a screw or similar mechanism, can be provided for mating the inner ends $86b_2$, $88b_2$ of each distal portion 86b, 88b to the actuating member 87. As shown in FIG. 8C, the mating element 95 has a portion (not shown) which is slidably disposed within the elongate slit 93.

In use, the expansion members 86, 88 are movable between a retracted position, shown in FIG. 8A, in which the return electrode 80 has a substantially elongate cylindrical shape, and an expanded position, shown in FIG. 8D. Movement of the actuating member 87 in a proximal direction causes the distal portion 86b, 88b of each expansion member 86, 88 to move from a substantially perpendicular position, , relative to the longitudinal axis l, to a substantially parallel position, and the proximal portion 86a, 88a of each expansion member 86, 88 to move inward toward the longitudinal axis l, as shown in FIG. 8A. Conversely, movement of the actuating member 87 in a distal direction causes the distal portions 86b, 88b to move from a substantially parallel position, to a position in which the distal portions 86b, 88b are substantially perpendicular to the longitudinal axis 1, and the proximal portions 86a, 88a of each expansion member 66, 68 to move outward away from the longitudinal axis l, as shown in FIGS. 8C and 8D.

Figures 9A, 9B:
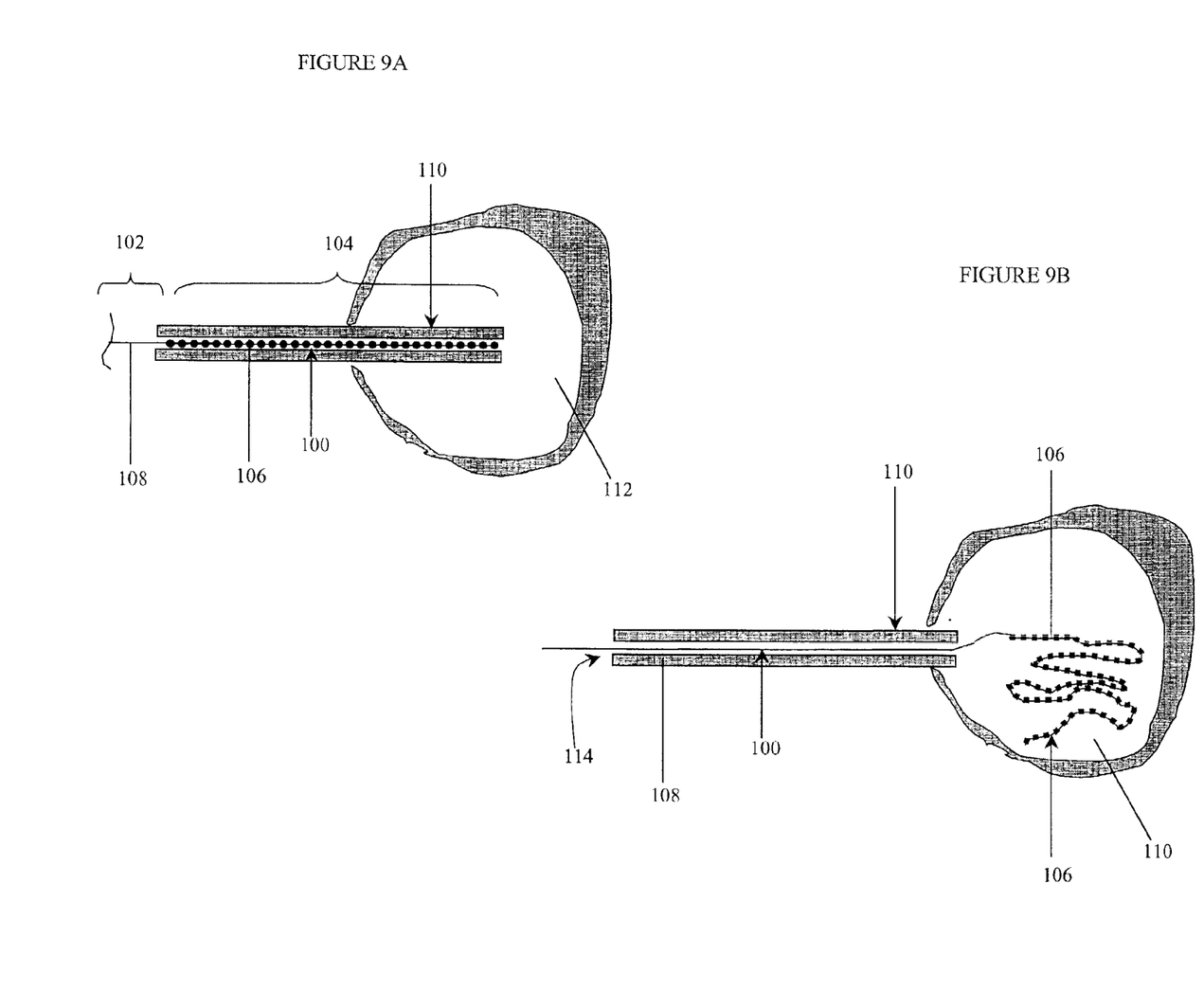
FIGS. 9A–9B illustrate another embodiment of an element movable between a first condition and a second, expanded condition that is useful in a system for treating atrial fibrillation.

FIGS. 9A–9B illustrate yet another embodiment of a return electrode 100. As shown, the return electrode 100 is a substantially elongate member having a proximal portion 102, a distal portion 104, and at least one discrete conductive element 106 disposed on the distal portion thereof. The return electrode 100 can be a substantially rigid member, or it alternatively can be flexible. The return electrode 100 can have a variety of configurations, but it is preferably formed from an elongate member 108, e.g., a wire, having the discrete conductive members 106 disposed thereon. The discrete conductive members 106 can be formed integrally with the elongate member 108, or they can be mated thereto using a variety of mating techniques. By way of non-limiting example, the discrete members 106 can be welded, adhesively secured, or mechanically connected to the elongate member 108.

The discrete members 106 can have a variety of configurations, but the discrete members 106 are preferably disposed adjacent to one another along the entire length of the distal portion 104. The shape and size of each discrete conductive member 106 can also vary. By way of non-limiting example, the discrete members can have a substantially spherical shape, a square shape, a rectangular shape, or virtually any other shape. While the size of each discrete member 106 can vary, the discrete members 106 preferably have a combined surface area that is greater than a surface area of the active electrode (not shown).

In use, the return electrode 100 can be inserted through tissue and positioned within or near a treatment site. In an exemplary embodiment, shown in FIGS. 9A and 9B, the return electrode 100 is inserted through an introducer element 110 and positioned within a treatment site 112. The introducer element 110 can have virtually any configuration, but it is preferably an elongate cylindrical member having an inner lumen 114 formed therein for slidably receiving the return electrode 100. During insertion of the return electrode 100 through the introducer element 110, the electrode 100 is in the retracted position, as shown in FIG. 9A, in which the return electrode 100 has a substantially elongate shape. Once positioned at the treatment site 112, the return electrode 100 is then free to move to the expanded position, shown in FIG. 9B, in which the distal portion 104 of the return electrode 100 has a substantially three-dimensional shape.

A person having ordinary skill in the art will appreciate that while FIGS. 5A–9B illustrate four different embodiments of the return electrode, the return electrode can have a variety of configurations. Moreover, the return electrode can include virtually any combination of features disclosed herein or known in the art.

While the embodiments shown in FIGS. 5A–9B are described as having an active electrode and a return electrode, a person having ordinary skill in the art will appreciate that the functionality of the electrodes can be reversed. For example, the return electrode can be adapted to be placed in contact with an epicardial surface of a heart, and the active, energy-delivering electrode can be selectively movable between a first, retracted position and a second, expanded position.

In another embodiment, the electrode element can serve as both an active and a return electrode, thereby having a bipolar configuration. By way of non-limiting example, two of the conductive elements 37a, 37d of the return electrode 30 illustrated in FIGS. 5A–5D can have a positive polarity, and the opposed conductive elements 37b, 37c can have a negative polarity. A person having ordinary skill in the art will appreciate that the positive and negative electrodes must be electrically insulated from each other to allow energy to transfer therebetween. In use, the conductive elements 37a, 37b, 37c, 37d are placed on a tissue surface, and energy is delivered between electrodes 37a and 37b, and electrodes 37c and 37d to form an ablative lesion on the tissue surface.

The present invention is intended to be deployed using any method that gives access to the heart. For example, the device can be deployed through a standard sternotomy, lateral thoracotomy, mini-thoracotomy, through small ports in an endoscopic port access procedure, or even percutaneously.

The following non-limiting examples serve to further describe the invention:

EXAMPLE 1

A patient is prepared for cardiac surgery in a conventional manner using conventional surgical techniques. The ablation procedure is performed on the patient's heart using a device having an active electrode and a return electrode in accordance with the present invention. A blood chamber in the heart, typically the left atria, is accessed using an atrial well. The return electrode is introduced into the atrial cavity through the atrial well, whereby the return electrode is retained in the retracted position. Once the return electrode is positioned in the desired region of the heart, the electrode is moved to the expanded position. The active electrode is then applied to an epicardial surface of the heart. Ablative energy can then be transmitted from the active electrode through the cardiac tissue and to the return electrode to form a lesion in the tissue.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entity.

What is claimed is:

1. A system for treating atrial fibrillation, comprising:
   an active, energy-delivering electrode being adapted to be placed in contact with a tissue surface for delivering energy effective to ablate tissue; and
   a return electrode selectively movable between a first, retracted position in which the electrode is adapted to be deployed through tissue, and a second, expanded position in which the electrode is adapted to be placed within a chamber of the heart, the return electrode having a surface area in the expanded position greater than a surface area of the active electrode.

2. The system of claim 1, further comprising an elongate member mated to the return electrode, the elongate member and the return electrode being adapted to be deployed through tissue when the return electrode is in the retracted position.

3. The system of claim 1, wherein the return electrode is formed from a shape-memory material and is biased to the expanded position.

4. The system of claim 1, further comprising a substantially elongate cylindrical member having an inner lumen formed therein, at least a portion of the return electrode being slidably disposed within the inner lumen of the cylindrical member.

5. The system of claim 4, wherein the return electrode is substantially disposed within the cylindrical member in the retracted position, and is adapted to assume the expanded position upon extension from the cylindrical member.

6. The system of claim 5, further comprising an actuating member mated to the return electrode for moving the return electrode between the retracted and expanded positions.

7. The system of claim 1, wherein the return electrode is a substantially elongate member having a proximal end and a distal end, the distal end being movable between the retracted and expanded positions.

8. The system of claim 1, further comprising an actuating member mated to the return electrode for moving the return electrode between the retracted and expanded positions.

9. The system of claim 1, wherein the active electrode is adapted to be placed in contact with an endocardial surface of a heart.

10. A method of forming a lesion at a predetermined heart location, comprising:
    providing an energy-delivering electrode;
    providing a return electrode selectively adjustable between a first condition and a second, expanded condition, the return electrode having a surface area in the expanded condition greater than a surface area of the energy-delivering electrode;
    positioning the return electrode within a chamber of the heart, and expanding the return electrode within the chamber; and delivering ablative energy through the energy-delivering electrode to the return electrode to form a lesion at the predetermined heart location.

11. The method of claim 10, wherein the return electrode is adapted to be deployed through tissue and into the chamber of the heart in the first condition.

12. The method of claim 11, wherein the return electrode has a substantially elongate cylindrical shape in the first condition.

13. The method of claim 10, wherein the return electrode has a size in the second, expanded condition that is less than a size of the chamber of the heart.

14. The method of claim 13, wherein the return electrode is positioned in contact with heart tissue in the chamber of the heart.

15. The method of claim 13, wherein the return electrode is free from contact with heart tissue in the chamber of the heart.

16. The method of claim 13, wherein the energy-delivering electrode is positioned on an epicardial surface of the heart.

17. A system for treating atrial fibrillation, comprising:

an active, energy-delivering electrode array having a plurality of distinct electrode elements adapted to communicate with a source of ablative energy and adapted to be placed in contact with a tissue surface; and a return electrode selectively movable between a first, retracted position in which the electrode is adapted to be deployed through tissue, and a second, expanded position in which the electrode is adapted to be placed within a chamber of the heart, the return electrode having a surface area in the expanded position greater than a surface area of the active electrode.

18. The system of claim 17, wherein the surface area of the return electrode is greater than a surface area of a single distinct electrode element on the active electrode.

19. The system of claim 18, wherein the electrode array is malleable.

20. A system for treating atrial fibrillation, comprising:

an active, energy-delivering electrode being adapted to be placed in contact with an epicardial surface of a heart; and a return electrode selectively movable between a first, retracted position in which the electrode is adapted to be deployed through tissue, and a second, expanded position in which the electrode is adapted to be placed within a chamber of the heart, the return electrode having a surface area in the expanded position greater than a surface area of the active electrode.

* * * * *